US011529039B2

(12) United States Patent
Brooks et al.

(10) Patent No.: US 11,529,039 B2
(45) Date of Patent: Dec. 20, 2022

(54) NON-CONDUCTIVE BORESCOPES AND RELATED IMAGING TECHNIQUES

(71) Applicant: Xenocor, Inc., Salt Lake City, UT (US)

(72) Inventors: Lane G. Brooks, Highland, UT (US); Christopher Joseph Pratt, American Fork, UT (US); Ashok C. Khandkar, Salt Lake City, UT (US); John T. Langell, Salt Lake City, UT (US); Dennis James Muhlestein, American Fork, UT (US)

(73) Assignee: Xenocor, Inc., Salt Lake City, UT (US)

( * ) Notice: Subject to any disclaimer, the term of this patent is extended or adjusted under 35 U.S.C. 154(b) by 458 days.

(21) Appl. No.: 16/407,059

(22) Filed: May 8, 2019

(65) Prior Publication Data

US 2019/0343371 A1    Nov. 14, 2019

Related U.S. Application Data

(60) Provisional application No. 62/668,705, filed on May 8, 2018.

(51) Int. Cl.
*A61B 1/00* (2006.01)
*A61B 1/06* (2006.01)
*A61B 1/05* (2006.01)

(52) U.S. Cl.
CPC ........... *A61B 1/00071* (2013.01); *A61B 1/05* (2013.01); *A61B 1/0684* (2013.01)

(58) Field of Classification Search
CPC ..... A61B 1/00071; A61B 1/0684; A61B 1/05; A61B 1/127; A61B 1/00009;

(Continued)

(56) References Cited

U.S. PATENT DOCUMENTS

| 3,294,085 | A |   | 12/1966 | Wallace |
| 5,311,859 | A | * | 5/1994 | Monroe ................. A61B 1/042 396/17 |

(Continued)

FOREIGN PATENT DOCUMENTS

| DE | 102009051434 A1 * | 5/2011 |
| WO | 2017217107 | 12/2017 |

OTHER PUBLICATIONS

Jul. 24, 2019 PCT/US/19/31381 International Search Report (2 pgs).
Jul. 24, 2019 PCT/US/19/31381 Written Opinion (5 pgs).

*Primary Examiner* — Timothy J Neal
*Assistant Examiner* — Sung Ham
(74) *Attorney, Agent, or Firm* — Matthew D. Thayne; Thayne and Davis LLC

(57) ABSTRACT

Borescopes and related methods that are configured to preclude or minimize imaging in hazy and/or smoky conditions. In some embodiments, the borescope may comprise a shaft made up, at least in part, of a material that is electrically non-conductive material and/or thermally non-conductive, and a tip positioned at a distal end of the shaft. The tip may comprise at least one light source, such as an LED or array of LEDS, configured to deliver electromagnetic radiation in which no more than about 20% of the total spectral output is in the infrared spectrum. The electromagnetic radiation delivered from the at least one light source may comprise a spectrum having at least one of a local maximum and a global maximum between about 450 and about 495 nm. The at least one light source may be configured to deliver between about 20 and about 75 lumens of visible light.

21 Claims, 10 Drawing Sheets

(58) Field of Classification Search
CPC ............ A61B 1/00011; A61B 1/00022; A61B 1/00057; A61B 1/00121; A61B 1/00124; A61B 1/00105; A61B 1/00108; A61B 1/01; A61B 2017/00057; A61B 2017/00061; A61B 2017/00066; H04N 2005/2255

See application file for complete search history.

(56) References Cited

U.S. PATENT DOCUMENTS

| | | | |
|---|---|---|---|
| 2001/0035902 A1 | 11/2001 | Iddan et al. | |
| 2005/0099824 A1* | 5/2005 | Dowling | A61B 90/36 362/572 |
| 2005/0281520 A1 | 12/2005 | Kehoskie et al. | |
| 2006/0069314 A1 | 3/2006 | Farr | |
| 2006/0106282 A1* | 5/2006 | Bala | A61B 1/0638 600/181 |
| 2007/0183162 A1* | 8/2007 | Higuchi | A61B 1/045 362/458 |
| 2008/0119694 A1* | 5/2008 | Lee | A61B 5/0075 600/127 |
| 2008/0208006 A1* | 8/2008 | Farr | A61B 1/0676 600/178 |
| 2010/0002292 A1 | 1/2010 | Yabe et al. | |
| 2011/0295066 A1* | 12/2011 | Fan | A61B 1/015 600/114 |
| 2013/0066165 A1* | 3/2013 | Shemer | A61B 1/0638 600/249 |
| 2014/0121468 A1* | 5/2014 | Eichenholz | A61B 1/0638 600/249 |
| 2014/0296628 A1* | 10/2014 | Kirma | A61B 5/064 600/103 |
| 2014/0309677 A1* | 10/2014 | Baldwin | A61B 17/128 606/1 |
| 2016/0088999 A1* | 3/2016 | Langell | A61B 1/00195 348/68 |
| 2016/0287063 A1* | 10/2016 | Ramanujam | A61B 1/00087 |
| 2017/0119490 A1* | 5/2017 | Mordaunt | A61B 3/0008 |
| 2017/0237960 A1* | 8/2017 | Kamm | H04N 5/2256 348/46 |
| 2018/0214206 A1* | 8/2018 | Thomas | A61B 18/1815 |
| 2019/0374285 A1* | 12/2019 | Hancock | A61B 5/0084 |
| 2021/0007591 A1* | 1/2021 | Weber | A61B 1/0684 |

* cited by examiner

NON-CONDUCTIVE BORESCOPES AND RELATED IMAGING TECHNIQUES

CROSS-REFERENCE TO RELATED APPLICATIONS

This application claims the benefit under 35 U.S.C. § 119(e) of U.S. Provisional Patent Application No. 62/668,705, which was filed May 8, 2018 and titled "NON-CONDUCTIVE BORESCOPES AND RELATED IMAGING TECHNIQUES," which is hereby incorporated herein by reference in its entirety.

SUMMARY

Embodiments of apparatus and methods are disclosed herein that relate, at least in preferred embodiments, to borescopes and other related medical borescopes, such as laparoscopy, endoscopy, and the like. In some embodiments disclosed herein, medical borescopes have one or more novel features that may be beneficial for imaging in certain condition, such as conditions with smoke or other particles in the air or otherwise within the vicinity of the object to be imaged. Some embodiments may additionally, or alternatively, provide for other improvements, such as reducing thermal conduction—which may decrease fogging—reducing or eliminating electromagnetic shielding requirements, and/or inhibiting electrical arcing during certain electrosurgical procedures. In some embodiments, one or more (in some embodiments, all three) of these features may be provided by manufacturing one or more portions of the borescope from an electrically (and, in some embodiments, thermally) non-conductive material, most preferably a fiber-reinforced, thermosetting polyester or other similar polymer.

In a more specific example of a borescope according to preferred embodiments, the borescope may comprise a handle and a tube or tubular portion and a tip at a distal end comprising one or more LEDs or other light sources, along with various other imaging elements, as described herein and/or available to those of ordinary skill in the art. The tube preferably at least partially comprises a material that is both electrically and thermally non-conductive, or at least substantially non-conductive. In preferred embodiments, this material comprises a fiber-reinforced, thermosetting polyester.

In some embodiments, one or more features may be provided that improve the ability of the borescope to image in conditions having particles and/or vapor in the imaging field, such as smoke from an electrosurgical procedure. Thus, in the specific example referenced above, the one or more LEDs may be configured to deliver electromagnetic radiation that is at least substantially lacking in infrared radiation and/or that has at least a local maximum (in some embodiments, a global maximum) in the blue region of the visible spectrum (i.e., between about 450 and about 495 nm).

In some such embodiments, the exemplary borescope referenced above may further be characterized in that the LED(s) deliver a lower overall amount of visible light than the typical laparoscopes. For example, the LED(s) may be configured to deliver between about 20 and about 75 lumens of light from all LEDs in the borescope. In certain more preferred embodiments of the exemplary borescope, the LEDs may be configured to deliver between about 25 and about 55 lumens of light.

In some embodiments, the exemplary borescope referenced above may further be characterized in that the aperture size leading to the image sensor, which may also be in the tip, may be larger than typical laparoscopes. Thus, in some embodiments, the aperture size may range from F2.0 to F2.8.

In a more particular example of a medical borescope according to some embodiments, the borescope may comprise a shaft, which may comprise a tube, comprising, at least in part, a material that is at least substantially electrically non-conductive material and at least substantially thermally non-conductive. For example, in some embodiments, the material may comprise an electrical conductivity less than about 20 S/m (Siemens per meter) and/or a thermal conductivity of less than about 10 W/mK (watts per meter-Kelvin) (in some such embodiments, both the aforementioned electrical and thermal conductivities). In some such embodiments, the material used may comprise an electrical conductivity less than about 5 S/m and/or a thermal conductivity of less than about 1 W/mK (in some such embodiments, both the aforementioned electrical and thermal conductivities).

The borescope may further comprise a tip positioned at a distal end of the shaft. The tip may comprise an image sensor configured to generate image data and one or more light sources, such as an array of LED light sources, configured to deliver electromagnetic radiation in a spectrum that is preferably at least substantially lacking in infrared radiation. In some embodiments and implementations, the spectrum may have at least one of a local maximum and a global maximum between about 450 and about 495 nm and/or the array of LED light sources may be configured to collectively deliver between about 20 and about 75 lumens of visible light.

In some embodiments, the shaft may wholly be made up of a material that is at least substantially electrically non-conductive material and at least substantially thermally non-conductive. In other embodiments, the shaft may comprise a layer of material, such as a coating or sheath, that is at least substantially electrically non-conductive material and at least substantially thermally non-conductive. In some such embodiments, the layer/coating may only be applied to a distal portion of the shaft adjacent to the tip and accompanying lighting and/or imaging components.

In some embodiments, shaft may be partially or wholly be made up of a fiber-reinforced material, such as a fiber-reinforced, thermosetting polyester polymer. In some embodiments, the fibers may run parallel to, or at least substantially parallel to, the axis of the shaft.

In some embodiments, the array of LED lights sources may be configured to deliver between about 25 and about 55 lumens of visible light.

In some embodiments, the tip may further comprise an imaging aperture comprising an aperture size between F2.0 and F2.8.

Some embodiments may be configured to deliver an electromagnetic spectrum having a global maximum between about 450 and about 495 nm.

In another example of a medical borescope according to some embodiments, the borescope may comprise a shaft comprising, at least in part (in some cases wholly), a material that is at least substantially electrically non-conductive material and at least substantially thermally non-conductive. Some embodiments may comprise a tip positioned at a distal end of the shaft. The tip may comprise at least one light source, such as one or more LEDs, configured to deliver electromagnetic radiation in which no more than about 20% of the total spectral output of the at least one light source is in the infrared spectrum and/or comprising a spectrum having at least one of a local maximum and a global maximum (in some embodiments a global maximum) between about 450 and about 495 nm. The at least one light source may be configured to deliver between about 20 and about 75 lumens of visible light.

In some embodiments, part or all of the shaft may comprise a fiber-reinforced polymer, such as a fiber-reinforced vinyl ester. More preferably, the fiber may comprise a unidirectional fiber, preferably aligned such that the fibers are oriented along the axis of the shaft.

In some embodiments, the material of the shaft, either in part or wholly, comprises an electrical conductivity less than about 5 S/m and/or a thermal conductivity of less than about 1 W/mK.

In an example of a method for medical imaging according to some implementations, the method may comprise inserting a medical borescope into a patient and illuminating a site of interest with electromagnetic radiation using between about 20 and about 75 lumens of visible light in an electromagnetic spectrum that is at least substantially lacking in infrared radiation. Preferably, the electromagnetic spectrum has at least one of a local maximum and a global maximum between about 450 and about 495 nm. The site of interest may then be imaged using illumination of the electromagnetic radiation.

Some implementations may further comprise performing a procedure in which smoke is generated, such as an electrosurgical procedure, wherein the electromagnetic spectrum is configured to at least substantially eliminate visibility of the smoke in one or more images generated during the imaging step.

In some implementations, the electromagnetic radiation may be generated using an array of LED light sources, which may be positioned on or otherwise adjacent to a tip of the medical borescope.

In some implementations, the array of LED lights sources may be configured to deliver between about 25 and about 55 lumens of visible light. The electromagnetic spectrum may have a global maximum between about 450 and about 495 nm.

The features, structures, steps, or characteristics disclosed herein in connection with one embodiment may be combined in any suitable manner in one or more alternative embodiments.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Figure 1:
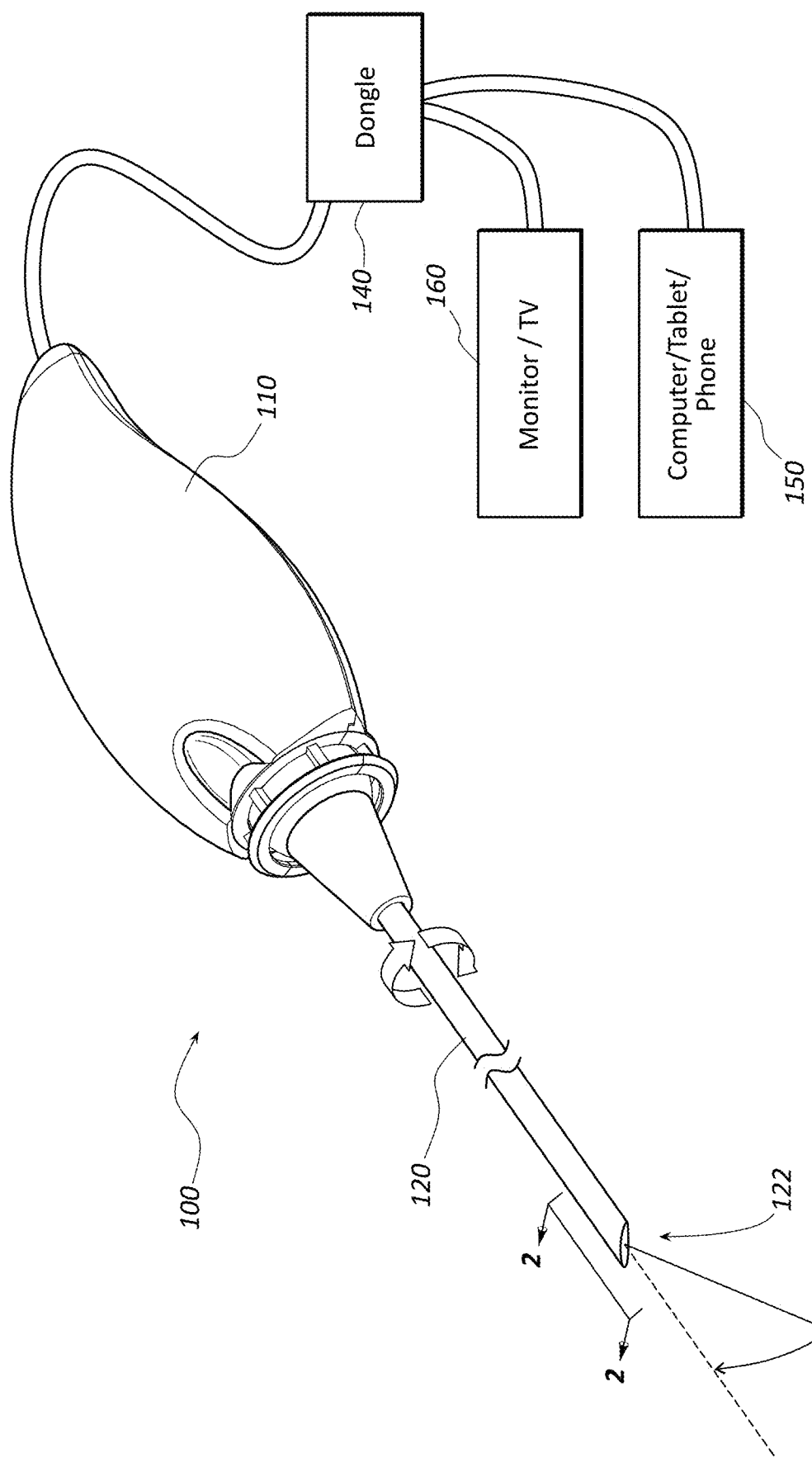
FIG. 1 depicts a borescope system according to some embodiments.

It will be readily understood that the components of the present disclosure, as generally described and illustrated in the drawings herein, could be arranged and designed in a wide variety of different configurations. Thus, the following more detailed description of the embodiments of the apparatus is not intended to limit the scope of the disclosure, but is merely representative of possible embodiments of the disclosure. In some cases, well-known structures, materials, or operations are not shown or described in detail.

Various embodiments of apparatus and methods are disclosed herein that relate to borescopes and other related medical borescoping, such as laparoscopy, endoscopy, and the like. The present inventors also anticipate possible uses of the inventive teachings provided herein in connection with certain industrial applications. In some embodiments disclosed herein, medical borescopes have one or more novel features that may be beneficial for imaging in certain condition, such as conditions with smoke or other particles in the air or otherwise within the vicinity of the object to be imaged.

In some preferred embodiments, the borescope may comprise a handle, a tube, and a tip at the distal end of the tube. The tip may comprise one or more light sources, such as LED lights, one or more image sensors, a lens assembly, and/or other medical borescope components. In some embodiments, the tip may further comprise a PCB and/or a memory element, such as a flash memory component or other non-volatile memory component, which may be used to store various types of data, such as the duration and/or number of uses of the device and/or model identification or calibration data, as described in U.S. patent application Ser. No. 14/958,728 titled MEDICAL BORESCOPES AND RELATED METHODS AND SYSTEMS, which was filed on Dec. 3, 2015 and is hereby incorporated herein by reference in its entirety.

As also described in the aforementioned patent application incorporated herein by reference, some embodiments may further comprise a dongle, which may be communicatively coupled with the device, such as by way of wires or by being plugged into the device, such as into a port formed within the handle of the device. This dongle may comprise a memory element and a processor, which may be used to process image data from an image sensor in the device. In some embodiments, the dongle may be removably coupled with the device so that it can be coupled with a plurality of distinct laparoscopes or other borescopes. For example, the dongle may comprise a data port that may be used to couple the dongle with a plurality of distinct borescopes and/or other devices, such as a general-purpose computer. In this manner, as discussed above, data obtained from the borescope, such as usage data, may be stored in the memory element of the dongle and ultimately transferred to another computer/device following a medical procedure.

In some embodiments, the device may further comprise a sensor that may be used to detect an orientation of a portion of the device. For example, some embodiments, may comprise a rotational position sensor configured to sense a rotational position of one portion of the device, such as the handle, with respect to another portion of the device, such as the tube and/or tip of the device. This may allow the device to be used in a manner similar to a traditional angled laparoscope but without requiring the camera to be rotatable with respect to the tube and/or maintained in a fixed orientation at the proximal end of the device during a surgical procedure.

In certain preferred embodiments, the camera/image sensor may be fixedly positioned in the tube. Thus, when the tube is rotated, the video stream/image inherently rotates with the tube. Thus, rather than using the optical rotation typically used by traditional laparoscopes, such embodiments may instead use digital rotation to mimic such optical rotation. In some such embodiments, a first portion of the device having the image sensor/camera, such as the tube, may be configured to rotate with respect to a second portion of the device, such as the handle, which may comprise a sensor, such as a rotational sensor, configured to sense a rotational orientation of at least a portion of the first portion with respect to at least a portion of the second portion. In this manner, the handle or another second portion of the device may act as the camera does in a traditional laparoscope. Thus, the doctor can maintain the handle/second portion in a fixed position while rotating the tube/first portion.

In preferred embodiments, the handle may comprise a rotational sensor configured to sense the position and/or rotational orientation of the handle with respect to the tube, which, again, may be rotatable with respect to the handle. The device may be configured such that this position/orientation data is used to perform digital manipulation/rotation to maintain a desired image/video stream orientation on a monitor or other display. In some embodiments, the dongle may receive the position/orientation data and may be configured to perform this manipulation/rotation, in some such embodiments along with the other image processing previously mentioned. Thus, in preferred embodiments, the dongle may be configured to capture a digital video stream from the camera/tip and process the raw image sensor data to convert it to a standard color HDMI or USB video stream for display on a monitor/TV or computer/tablet/phone and may also be configured with circuitry to control the LED or other light source, the exposure level of the image sensor, and/or the rotational orientation of the video stream. This digital manipulation/rotation may be used to preserve the rotational orientation between the tube and the handle, or between two other portions of the device, to allow the camera/sensor to be fixed with respect to the tube and preserve the behavior of optical rotation that many surgeons are accustomed to.

Some preferred embodiments and implementations may also, or alternatively, comprise a non-conductive material, such as a plastic, elastomeric, or ceramic material, that may serve as an electromagnetic shield from other devices, such as cauterization devices or other electrosurgical devices. Such material may make up the entire tube portion, or a portion of the tube. More specific materials that the present inventors have discovered to be particularly useful for this purpose, without unduly sacrificing other desired functionality for a medical borescope, include certain high-strength polymers, such as polycarbonate or polyether ether ketone (PEEK). In some embodiments, a shielding tube may be positioned concentrically over another tube. In some embodiments, other shielding techniques/features, such as a Faraday cage, may be incorporated within or otherwise adjacent to the non-conductive tube or tube portion. However, by incorporating the materials disclosed herein into the medical borescope, and particularly the tube portion of the borescope, shielding requirements for the device may be reduced or eliminated.

Such non-conductive materials also may provide other benefits, such as reducing or eliminating the incidence of electrical arcing during certain procedures, such as electrosurgical procedures. Thus, some embodiments may further comprise one or more lumens configured to receive and deliver electrosurgical energy, such as energy used to cauterize tissue during an electrosurgical procedure or to cauterize blood vessels or other tissue after another surgical procedure. Alternatively, a separate electrosurgical device may be used along with one of the inventive laparoscopes or other borescopes disclosed herein, in which case at least a portion of the borescope device, such as the shaft of the borescope device or, in some embodiments, the entire borescope device, may be composed of electrically non-conductive material in order to inhibit electrical arcing and/or other problems that may be caused by use of conductive materials adjacent to an electrosurgical device.

Such a procedure may be viewed by the image sensors also disclosed herein before, during, and/or after the procedure. Thus, by providing a tube that is preferably wholly, less preferably wholly along at least a portion of the axis, and less preferably at least partially, non-conductive may inhibit injury to a surgeon or others that may result from electrosurgical energy travelling from the tip of an endoscope or other borescope, down the tube, and into the surgeon or otherwise into an undesirable location. Although providing the entire tube and/or shaft of the device with a non-conductive material, and more preferably the specific materials disclosed herein, may be preferred, it is contemplated that some of the benefits discussed herein may be achieved by coating the tube with such a material or otherwise forming a layer of such material over other material, which other material may include metallic or otherwise electrically and/or thermally conductive material. In a specific example, a sheath, such as a polyolefin or other elastomeric, non-conducting sheath, may be applied to a portion of the shaft or the entire shaft, which may be considered another example of a layer of non-conductive material.

Still another benefit may be provided by use of one or more of the preferred, non-conductive materials disclosed herein. Electrically conductive materials are known to often be thermally conductive as well. Metals and other thermally conductive materials may suffer from drawbacks due to the thermal conductivity. For example, by allowing thermal energy from the colder, operating room temperature to travel to the tip or otherwise in the vicinity of the image sensor, which is typically much warmer (at or near the normal body temperature of the patient, condensation of moisture and fogging may take place. Thus, it may be preferable to provide at least a portion of the borescope using a thermally non-conductive material.

For this purpose, it may be sufficient to provide a thermally-insulating barrier that does not consist of making the entire tube from a thermally non-conductive material. For example, in some embodiments, only a portion of the tube and/or another portion of the borescope, such as the handle, is made from a thermally non-conductive material. However, it still may be preferred to make the entire tube, or in some such embodiments, the entire handle and/or entire borescope including handle and tube, from a thermally and preferably electrically non-conductive material, since doing so may reduce thermal conduction, which, again, may decrease fogging, as well as provide electromagnetic shielding and inhibit arcing, as mentioned above.

For certain applications and/or purposes, it may be most desirable to ensure that the portion of the borescope adjacent to the imaging components, such as the image sensor, light source, etc., be defined, either partially or wholly, by one or more of the preferred non-conductive materials disclosed herein. Thus, it is contemplated that, in some embodiments in which these elements may be in the tip of the device, only a distal portion of the tube adjacent these elements may be made up of the polymer or other non-conductive material.

In preferred embodiments, the non-conductive material comprises a fiber-reinforced polymer, such as a fiber-reinforced thermosetting polymer. In more preferred embodiments, the non-conductive material comprises a fiber-reinforced thermosetting polyester, such as a fiber-reinforced vinyl ester. In an even more preferred embodiment, the fiber-reinforced thermosetting polyester comprises a unidirectional fiber, preferably aligned such that the fibers are oriented along the long axis of the tube of the device. In some embodiments, the tube of the device may be composed of a C-fiber reinforced material. In some embodiments, the fibers may be oriented in a cross-ply direction, or in combination with unidirectional orientation to maximize the strength and stiffness of the shaft/tube for a given cross section. Again, in preferred embodiments, these fibers are unidirectional and also preferably oriented along the axis of the tube portion. Although these materials are most preferably used in the tube portion of the device, it is contemplated that they may be used in other portions of the device, such as the handle and, in some embodiments, the entire laparoscope or other borescope.

Thus, by using a material that is both electrically and thermally non-conductive and by placing the material in proper locations, as discussed above, a laparoscope or other borescope may be provided that avoids or at least reduces the problems or electrical arcing, fogging, and may reduce or eliminate the need for EMF shielding. In some preferred embodiments, the material used may comprise an electrical conductivity less than about 20 S/m (Siemens per meter) and/or a thermal conductivity of less than about 10 W/mK (watts per meter-Kelvin) (in some such embodiments, both the aforementioned electrical and thermal conductivities). In more preferred embodiments, the material used may comprise an electrical conductivity less than about 5 S/m and/or a thermal conductivity of less than about 1 W/mK (in some such embodiments, both the aforementioned electrical and thermal conductivities).

Other novel aspects of certain embodiments of borescopes are also disclosed herein, such as camera/camera module coupling methods and assemblies, methods and structures for heat dissipation, providing for increased resolution video streams, specific methods for detecting rotational position/orientation, and related improvements.

The embodiments of the disclosure may be best understood by reference to the drawings, wherein like parts may be designated by like numerals. It will be readily understood that the components of the disclosed embodiments, as generally described and illustrated in the figures herein, could be arranged and designed in a wide variety of different configurations. Thus, the following detailed description of the embodiments of the apparatus and methods of the disclosure is not intended to limit the scope of the disclosure, as claimed, but is merely representative of possible embodiments of the disclosure. In addition, the steps of a method do not necessarily need to be executed in any specific order, or even sequentially, nor need the steps be executed only once, unless otherwise specified. Additional details regarding certain preferred embodiments and implementations will now be described in greater detail with reference to the accompanying drawings.

FIG. 1 depicts a borescope 100 according to some embodiments. As shown in this figure, borescope 100 comprises a handle 110, a tube 120, and a tip 122 at the distal end of tube 120. Although not visible in FIG. 1, preferably tip 122 comprises an image sensor, a lens, one or more light sources, a microprocessor, power management chips, and/or a memory component. Preferably, the tip is configured to digitize the images/video stream and control the LED or other light source illumination. Also, in the preferred embodiment of FIG. 1, tip 122 comprises an angled tip, which improves the ability to control image selection during a surgical procedure, as indicated by the angle referenced in FIG. 1. The angle of angled tip 122 may vary as desired. For example, in some preferred embodiments, this angle may be thirty degrees and therefore borescope 100 may be considered a "30-degree scope."

As shown by the arrows in FIG. 1, preferably the tube 120 is configured to rotate with respect to the handle 110. Thus, preferably the handle comprises a sensor configured to detect a rotational orientation of the handle with respect to the tube. It is contemplated, however, that in alternative embodiments the tube may instead comprise such a rotational sensor. It is also contemplated that other portions of borescope 100 may be rotatable with respect to one another and/or comprise such a rotational sensor in still other alternative embodiments.

A dongle 140 may be communicatively coupled with handle 110. Although the figure depicts a wire extending between these two elements, as described in the incorporated patent application referenced above, in alternative embodiments dongle 140 may simply plug into handle 110 or into another suitable portion of borescope 100.

Dongle 140 may, in turn, be communicatively coupled with a mobile general-purpose computing device 150, such as a computer/tablet/phone and/or a display 160, such as a TV or monitor. Again, although cables/wires are depicted in the figure, such as HDMI and/or USB cables, it is contemplated that any other suitable coupling techniques/structures may be used as desired. For example, in some embodiments and implementations, the dongle 140 may be unplugged from handle 110 and plugged into the mobile general-purpose computing device 150 and/or display 160 as needed.

Figure 2:
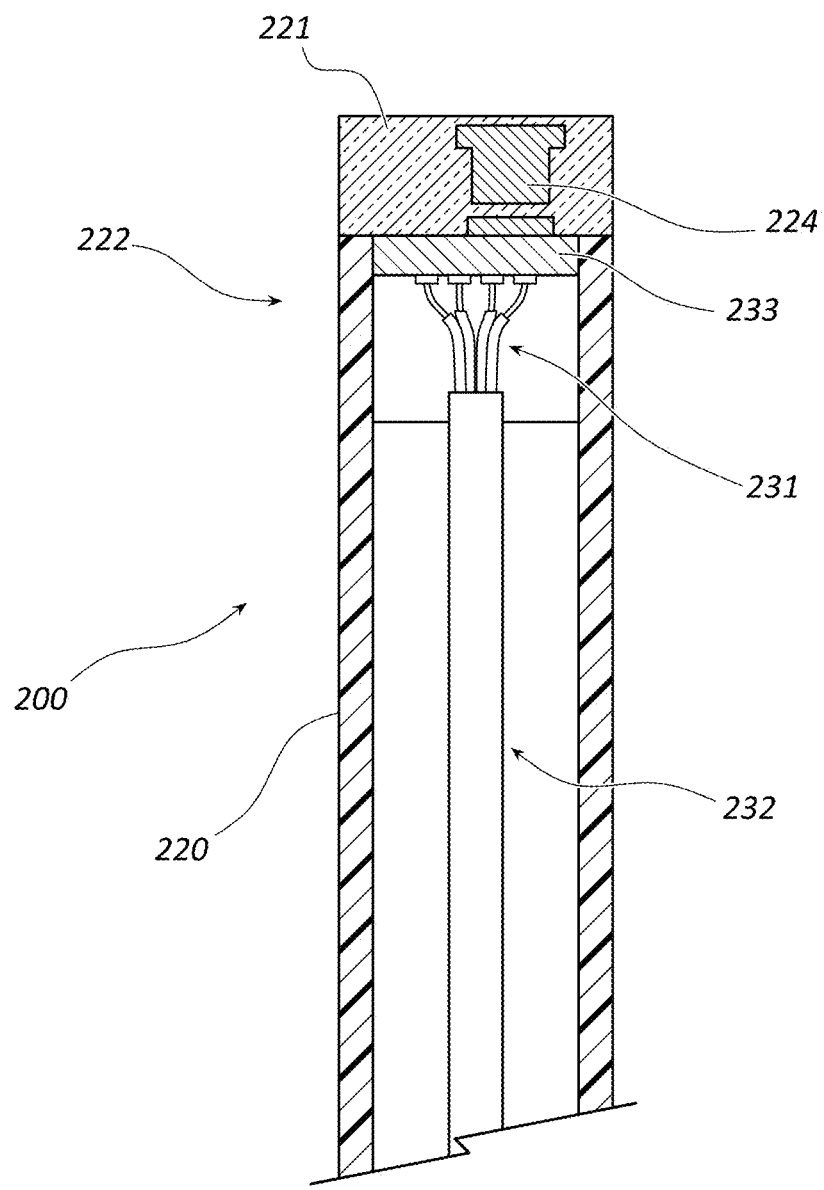
FIG. 2 depicts the distal end of a borescope according to some embodiments.

FIG. 2 illustrates a portion of a second embodiment of a borescope 200. More particularly, FIG. 2 depicts the distal end or tip 222 of tube 220 of borescope 200. In this embodiment, a camera module 221, which may comprise a lens and/or imaging assembly 224, is sealed to the distal end of tube 220. Thus, in this embodiment, the camera module 221 is external to the tube 220 and may require a seal, such as an epoxy or other adhesive, between the distal end of tube 220 and the camera module. The distal end of the tube 220 in this embodiment may comprise a PCB 233 and a potting 231 of the coupling of wires 232 with PCB 233. Although not shown in FIG. 2, wires 232 may be coupled with a dongle or a port configured to receive such a dongle.

Figure 3:
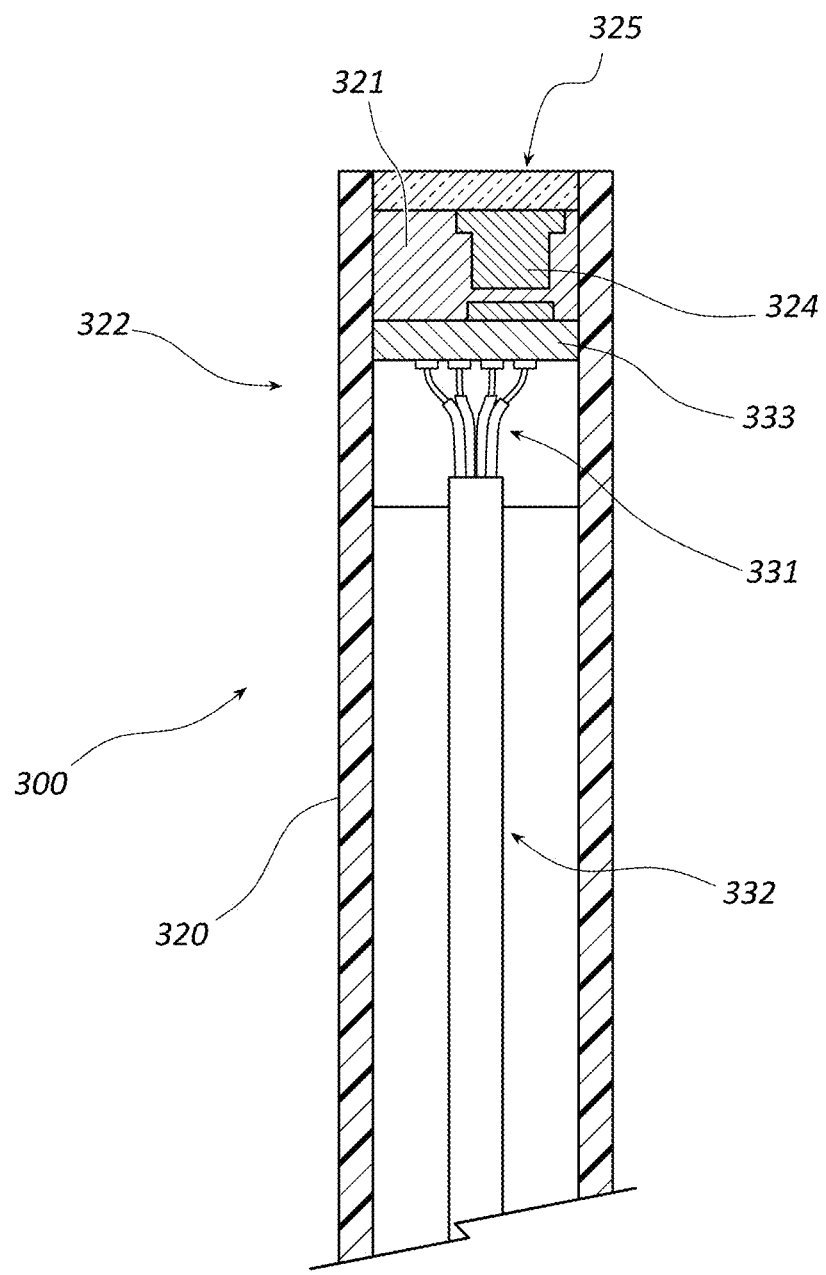
FIG. 3 depicts the distal end of a borescope according to other embodiments.

FIG. 3 depicts the distal end or tip 322 of tube 320 of an alternative embodiment of a borescope 300. In this embodiment, the camera module 321, which again may comprise a lens and/or imaging assembly 324, is positioned inside of tube 320 rather than sealed to the distal end of the tube as in borescope 200. Thus, camera module 321 may be inserted into the tube 320 and sealed in place, such as, for example, by using a suitable epoxy or other adhesive, within an adhesive reservoir 325 formed at the distal end of tube 320. This may result in an improvement of the seal relative to the design of FIG. 2. For example, even without controlled dispensing of the epoxy, an operator can fill the reservoir and visually see whether the seal fill is uniform. This may also improve the integrity and stability of the attachment of cameral module 321.

As with borescope 200, borescope 300 may further comprise a PCB 333 and a potting 331 of the coupling of wires 332 with PCB 333.

It is contemplated that, in some embodiments, the LED(s)/light source(s) and image sensor(s) may be positioned on a single PCB and encapsulated using a curable adhesive. However, this configuration may, in some embodiments, result in undesirable image sensor heating. Thus, in alternative embodiments, the LED(s)/light source(s) may be positioned on separate PCBs relative to the image sensor(s). In some embodiments, a housing, such as a lens housing, may then be used as the encapsulating feature rather than a curable adhesive.

In some preferred embodiments, a high-resolution image sensor may be used, such as, for example, an image sensor with a resolution of 1920×1080 with 1.4×1.4 μm pixels. Other embodiments may instead utilize lower resolution sensors, such as a 1280×720 image sensor with 1.75×1.75 μm pixels. In some embodiments, a plurality of image sensors and/or lens assemblies may be configured to be interchanged with one another in the borescope. However, because use of a 1080p sensor doubles the number of pixels with the same frame rate (e.g., 30 fps) relative to a 720p borescope, an unused differential pair in the cable may be provided to carry an additional serial stream so that the bandwidth requirements of the serial lines do not increase.

Figure 4:
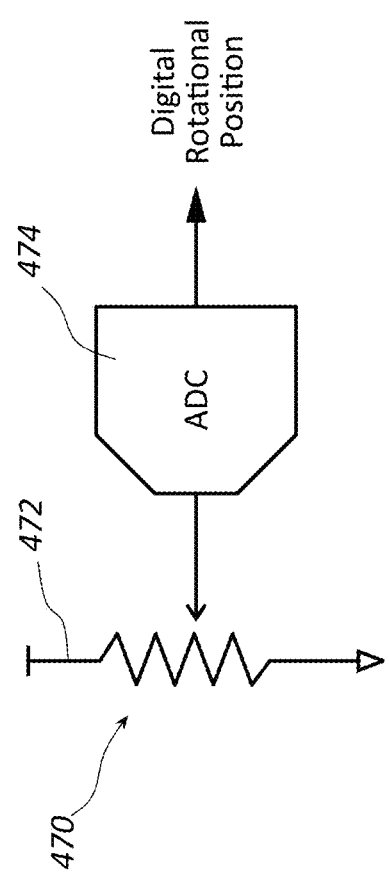
FIG. 4 depicts an example of the circuitry for a sensor for use in detecting a rotational position of a portion of a borescope with respect to another portion of the borescope.

A schematic example of a rotational sensor 470 suitable for use in connection with one or more of the borescopes disclosed herein is depicted in FIG. 4. As previously mentioned, in preferred embodiments, sensor 470 may be positioned in the handle of the device, and the tube may be rotatable with respect to the handle. Preferably, the sensor 470 is configured to sense the rotational position/orientation of the tube with respect to the handle. However, as previously mentioned, alternative embodiments are contemplated in which the sensor 470 may be located elsewhere and/or other portions of the device may be rotatable with respect to one another.

As shown in FIG. 4, in some embodiments, sensor 470 may comprise a potentiometer or other voltage divider circuit 472 and an analog to digital convertor (ADC) 474. The wiper of the potentiometer 472 may be configured to move as the tube of the borescope rotates, which creates a voltage proportional to the amount/degree of rotation. This voltage may then be fed to the ADC 474, as shown in FIG. 4, to digitize the voltage and perform digital rotation of the images of the borescope, which may allow for preserving the rotational orientation of the video stream even as the tube and therefore the camera/image sensor on the distal end of the tube are rotated during a surgical procedure.

Those of ordinary skill in the art will appreciate, however, that the sensor 470 of FIG. 4 is for purposes of illustration and a variety of other sensors/solutions may also be provided for digital re-orientation of video and/or images from a borescope. For example, other possible solutions include a shaft encoder or a single-turn rotational potentiometer, which may be attached to the tube.

Figure 5:
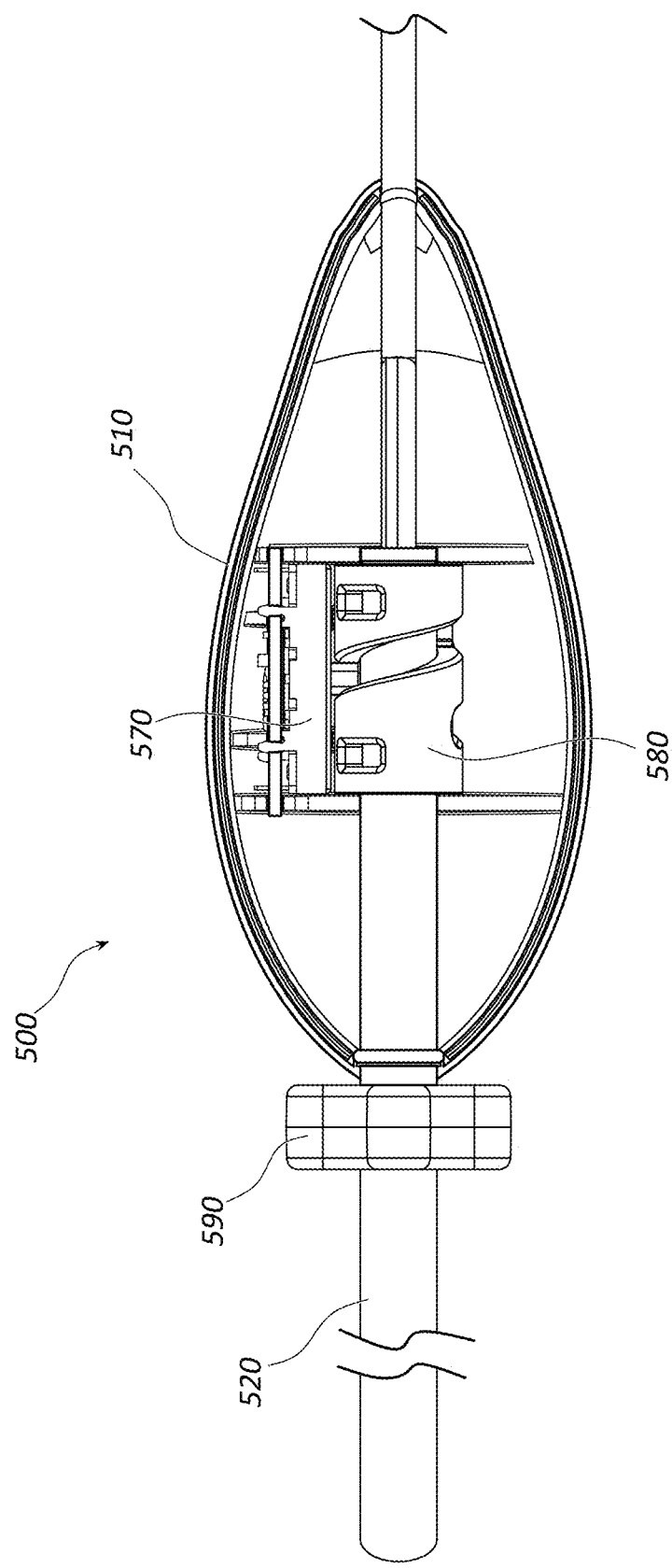
FIG. 5 depicts the interaction between a rotatable shaft and a handle of a borescope according to some embodiments.

FIG. 5 illustrates in more detail the structure of the handle 510 of a borescope 500 and, more particularly, the coupling between the handle 510 and the tube 520, that may allow for the sensor 570 to operate in a desired manner. As shown in this figure, handle 510 may comprise a potentiometer 570 or other sensor and a rotational coupling element 580, such as a worm gear, which may be coupled with the sensor 570 to allow the tube 520 to rotate with respect to the handle 510 and to allow the rotational position to be translated into a linear position and sensed by the potentiometer 570 or other sensor. In some embodiments, tube 520 may be integrally configured with a worm gear or other rotational coupling element 580. A tip, which may be angled, and may comprise any of the various elements previously discussed or otherwise available to those of ordinary skill in the art, such as lighting, imaging, memory, and/or processing elements and/or modules containing such elements, may be positioned at the distal end of shaft/tube 520.

A rotational dial or grip 590 may also be formed adjacent to handle 510 to facilitate manual rotation of tube 520 with respect to handle 510. Rotational dial or grip 590, which may comprise an annular structure extending about a desired portion of tube/shaft 520 (a portion abutting the distal portion of handle 510 in the depicted embodiment) may be fixedly coupled to tube/shaft 520 and therefore rotatably coupled to handle 510 (by virtue of the rotational coupling of tube/shaft 520 with respect to handle 510) to provide a surface to improve the ability of a surgeon/operator to rotate tube/shaft 520 with respect to handle 510. Dial/grip 590 may comprise various other features, such as bumps, knobs, grooves, a roughened surface, and/or the like to further facilitate desired.

In other embodiments, the shaft/tube 520 may be manufactured with an external groove, which may be used instead of a worm gear for a similar purpose. In still other embodiments, a twist potentiometer may be used instead of a slide potentiometer. Such an alternative potentiometer may be, for example, coupled directly to the shaft/tube 520, either on the proximal end or on the side via another gear mechanism. In other embodiments, a direct gear may be used to couple to a rotational potentiometer, a hall-effect sensor may be used for shaft encoding, and/or an optical shaft encoder may be used. Each of these is an example of means for sensing rotation between a first portion of a borescope and a second portion of a borescope rotatable with respect to the first portion.

In some embodiments, the sensor reading may be converted to a rotation angle by calibrating each borescope. These calibration settings may, in some embodiments, be stored in a storage element in the borescope, such as in the tip. Thus, in some embodiments, a plurality of calibration points (four, for example) may be stored and interpolation may be used for angle readings in between the calibration points.

It is contemplated that, in alternative embodiments, the ADC for the potentiometer 570 may be positioned in the tip and/or tube of the borescope. In some such embodiments, a two-conductor cable may be used to deliver the analog voltage from the potentiometer in the handle down the tube to the ADC in the tip/tube. However, the present inventors have discovered that this analog voltage may be susceptible to interference from EM radiation during electrocautery procedures. Thus, for certain applications, it may be preferable to position the ADC and the circuitry for the potentiometer 570 or other sensor in the handle 510 and instead transmit the digital signal from the handle 570 (either to the tip or directly to a dongle, for example) following conversion of the signal. This configuration may provide the benefit of elimination, or at least substantial reduction, of EM interference caused by electrocautery.

As previously mentioned, some embodiments may comprise a wire/cable that runs from the tip of the borescope through the tube and either out the handle or terminating in the handle. The present inventors have further discovered that, because in preferred embodiments the tube may be configured to rotate with respect to the handle, and because the wire/cable is preferably secured to the inside of the handle, the wire/cable must absorb the rotation over its length with appropriate strain relief. For this reason, it may be preferred to limit the ability of the handle to rotate with respect to the tube to a predetermined amount. For example, in some embodiments, the worm gear 580 or another suitable component may be used to limit such rotation to no more than a single, complete rotation. In some such embodiments, the rotation may be limited to less than a full rotation such as, for example, a quarter rotation in either direction. In alternative embodiments, the tube/shaft may be configured to rotate continuously in either the clockwise or counter-clockwise directions without any limit on the degree or number of rotations.

Figure 6:
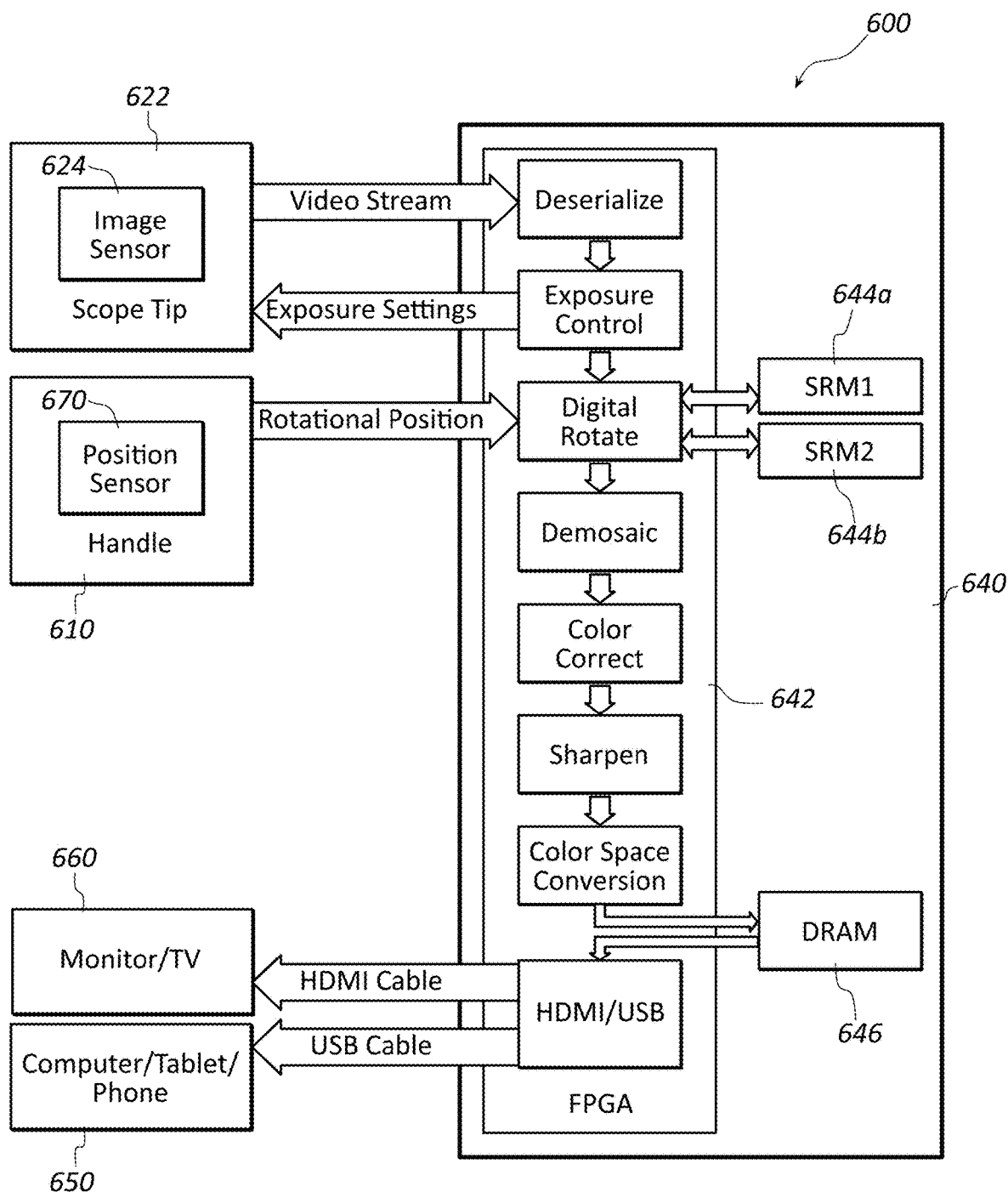
FIG. 6 is a schematic diagram of a borescope system according to some embodiments.

FIG. 6 is a block diagram illustrating various aspects of a preferred embodiment of a borescope 600 comprising a handle 610, a tip 622 at the end of a shaft/tube, and a dongle 640. As previously mentioned, tip 622 may comprise an image sensor 624. Although not shown in FIG. 6, various other elements may also be positioned in tip 622, such as one or more light sources, such as LED lights, one or more image sensors, a lens assembly, a PCB, and/or a memory element, such as a flash memory component or other non-volatile memory component.

As also previously mentioned, a sensor 670, such as a position sensor, may be provided. In preferred embodiments, position sensor 670 may be positioned in handle 610 and handle 610 may be rotationally coupled to the tube/shaft of the borescope 600. Thus, position sensor 670 may be configured to detect the rotational position of the handle 610 with respect to the tube/shaft and/or tip 622 so that the image(s) and/or video stream from image sensor 624 may be digitally manipulated to rotate them into a desired configuration during use.

As shown in FIG. 6, the image data, such as a video stream, may be transferred from image sensor(s) 624 in the scope tip 622 to the dongle 640, such as a Field Programmable Gate Array (FPGA) 642 of the dongle 640. The FPGA 642 may be configured to serialize the image data and apply one or more settings to the scope tip, such as exposure settings. Positional data, such as rotational position data, may be transferred from position sensor 670 to dongle 640. Digital rotation/manipulation of the image data may then be performed using the serialized image data and the rotational position data from sensor 670.

In performing digital rotation of the image data, it may be desired to achieve as low-latency rotation as possible at the full frame rate. Low latency is desired for at least two reasons. First, latency affects the ability of the surgeon to perform real-time surgery. Delay in the video stream could cause over-correction, tool misplacement, etc. Second, it may be desired to mimic the optical rotation of a traditional laparoscope, as previously mentioned. The optical rotation of traditional laparoscope does not typically introduce any latency.

In order to maintain a desired frame rate while eliminating or at least reducing latency, digital rotation may utilize a high-speed random access frame buffer. For example, under 0-degree image rotation the pixels would be read out of the frame buffer sequentially. However, in the case of a 90-degree image rotation, a pixel is read from a given row and then must access columns from non-sequential locations or from locations that are not co-located with each other. In such embodiments, access is not required to be sequential.

Although it is contemplated that some embodiments may utilize DRAM for frame buffering, doing so may introduce difficulties in providing high-speed random access for real-time image rotation. Preferred embodiments may therefore instead comprise two high-speed SRAM's in a double buffer fashion to achieve real-time digital rotation. Thus, as shown in FIG. 6, dongle 640 may comprise a first SRAM 644a and a second SRAM 644b that may, in conjunction with FPGA 642 and the positional data of sensor 670, together provide real-time or near real-time digital rotation of the image data from image sensor 624. More particularly, in some implementations, one SRAM 644a may receive the current frame while the second SRAM 644b is reading and rotating the previous frame. Then, the role of the SRAMs 644 is reversed (SRAM 644b receives the current frame and SRAM 644a reads and rotates the previous frame) when the frame is complete. This enables real-time digital rotation while adding only one frame of latency, which is acceptable and considered "real time" for most surgical applications.

In some embodiments, a dedicated Graphical Processing Unit (GPU) may be provided in place of the two, discrete SRAM units 644a and 644b. While a GPU may be able to perform real-time image rotation efficiently due to its utilization of integrated high-speed SRAM, it also adds expense. Thus, for certain applications, it may be preferable to use discrete SRAMs, as shown in FIG. 6, as a more cost-effective method of obtaining real-time, low-latency digital image rotation.

As also shown in FIG. 6, various other processing steps may be performed by dongle 640, such as demosaicing, color correction, sharpening, and/or color space conversion. One or more of these steps may be performed using a DRAM unit 646. Following digital rotation and processing of the image stream, the stream may be delivered to, for example, a display 660, such as a monitor or TV, to a mobile general-purpose computing device 650, such as a computer, tablet, or smart phone, or both. In some embodiments, the dongle may comprise common, universal, and/or non-customized display connectors such as HDMI or USB, for example, such that a common, non-customized, non-proprietary display, such as a display from a mobile general-purpose computing device may be used to display images from the device. Although cables are shown in the schematic diagram of FIG. 6, it should be understood that alternative embodiments are contemplated in which the delivery of processed image data may take place wirelessly or by way of suitable connectors, such as preferably the common, universal, and/or non-customized display connectors mentioned above, and internal wires/cables only.

Figure 7:
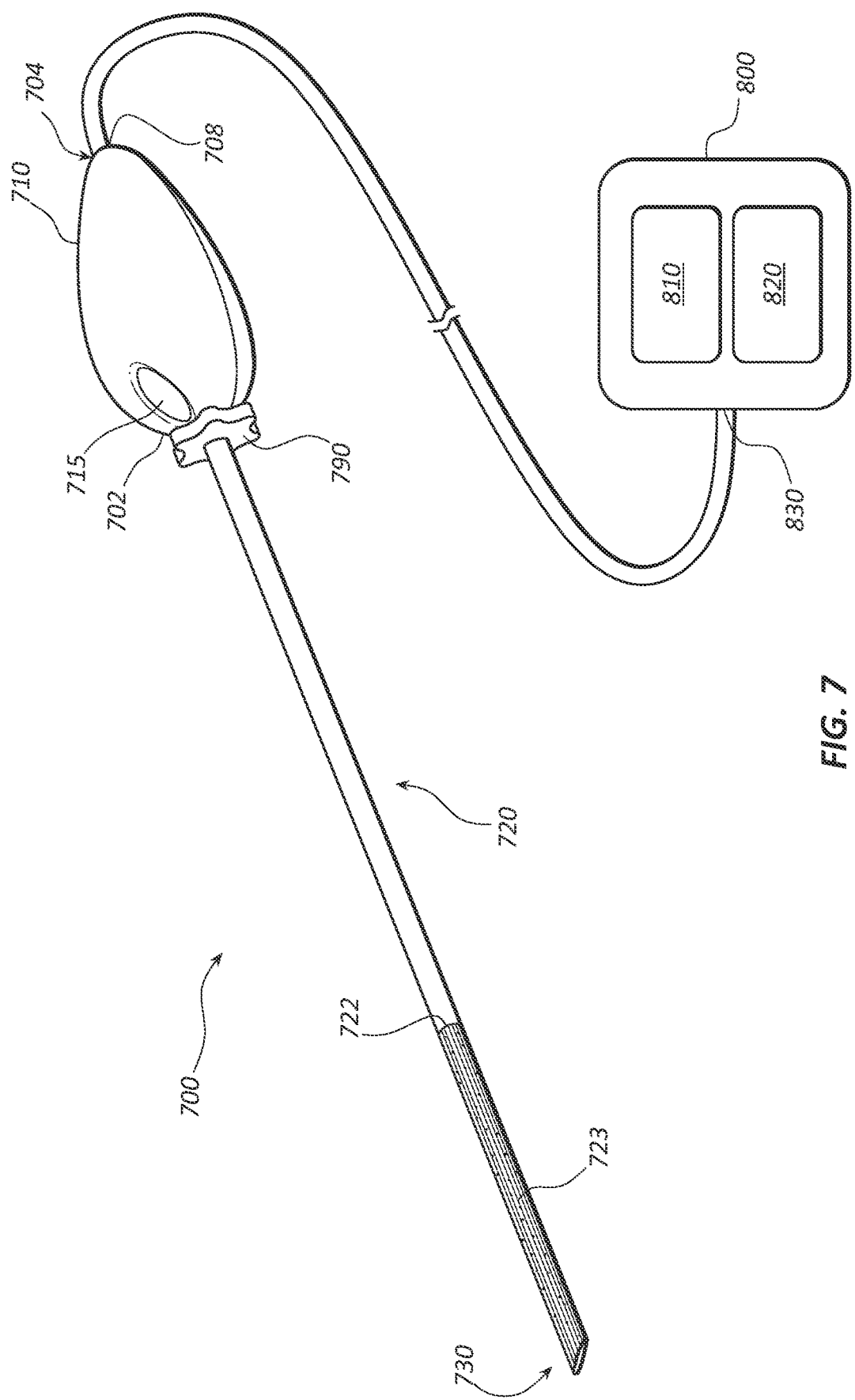
FIG. 7 is a perspective view of a borescope having a non-conductive tube according to certain embodiments.

FIG. 7 depicts another embodiment of a borescope 700. Borescope 700 comprises a handle having a distal end 702, from which a borescope shaft 720, which may comprise a tube, extends. In preferred embodiments, borescope shaft/tube 720 comprises a non-conductive material, such as polycarbonate or polyether ether ketone (PEEK). In more preferred embodiments, borescope shaft/tube 720 comprises a fiber-reinforced polymer, such as a fiber-reinforced thermosetting polymer. In still more preferred embodiments, the non-conductive material comprises a fiber-reinforced thermosetting polyester, such as a fiber-reinforced vinyl ester. In an even more preferred embodiment, the fiber-reinforced thermosetting polyester comprises a unidirectional fiber, preferably aligned such that the fibers are oriented along the long axis of the tube of the device, as shown at 723 in FIG. 7. In some embodiments, the tube of the device may be composed of a C-fiber reinforced material. Again, in preferred embodiments, these fibers are unidirectional and also preferably oriented along the axis of the tube portion.

As previously mentioned, in preferred embodiments, the entire shaft/tube 720 may comprise one of the aforementioned fiber-reinforced, thermosetting polymers or other preferred non-conductive materials discussed herein. However, in alternative embodiments, only a portion of the shaft/tube 720 may comprise such a material and the rest of the material may comprise an electrically conductive material.

For example, in the depicted embodiment, shaft/tube 720 may comprise a distal portion and a proximal section. These two sections may be separated along line 722. The distal section may be made up entirely of the preferred, non-conductive material or may comprise a coating, sheath, and/or other layer of the non-conductive material. Of course, this layer may, in some embodiments, extend along the entire shaft/tube 720. Thus, although it may be preferred to define the entire shaft/tube 720 with one or more of these non-conductive materials, preferably at least a portion of the portion of shaft/tube 720 adjacent to tip 730, which, as discussed below, may comprise various imaging components, is defined by such materials.

Borescope 700 further comprises a proximal end 704. Borescope 700 further comprises a dongle 800 that can be coupled, in preferred embodiments removably coupled, with handle 710 or otherwise with the body of borescope 700. For example, a port 708 may be formed at proximal end 704 of handle 710 and a similar port 830 formed on dongle 800, one or both of which may be pluggable to allow dongle 800 to be removed from borescope 700 and potentially be recoupled with another borescope. Thus, in some embodiments, borescope 700 may be disposable and dongle 800 may be reusable.

Dongle 800 further comprises a memory element 810, and a processor 820, which, as discussed above, may be used to process image data from an image sensor in the borescope 700, as discussed above. Dongle 800 further comprises a data port 830, which may be used to couple dongle 800 with borescope 700 and, in some embodiments, may also allow dongle 800 to be coupled with another device, such as a general-purpose computer. In this manner, as discussed above, data obtained from borescope 700, such as usage data, may be stored in memory element 810 and ultimately transferred to another computer following a medical procedure.

The handle of borescope 700 further comprises a narrowed stem 710 adjacent to the proximal end 704, which may allow a user to confirm, by either tactile or visual inspection, that the handle is in a desired rotational orientation during a procedure, as previously mentioned. A recess 715 may be positioned on the handle body, such as on a lower or, in the depicted embodiment, upper surface of the handle body. Recess 715 may provide the ability to confirm by either tactile or visual inspection that the handle body 700 is in a desired rotational orientation during a procedure by simply feeling with an index or other finger, for example. Borescope 700 further comprises a rotational dial or grip 790 that is shown formed adjacent to the distal end of handle 710 (but may be formed on the proximal end or elsewhere in alternative embodiments) to facilitate manual rotation of shaft/tube 720 with respect to handle 710, as previously discussed.

Figure 8:
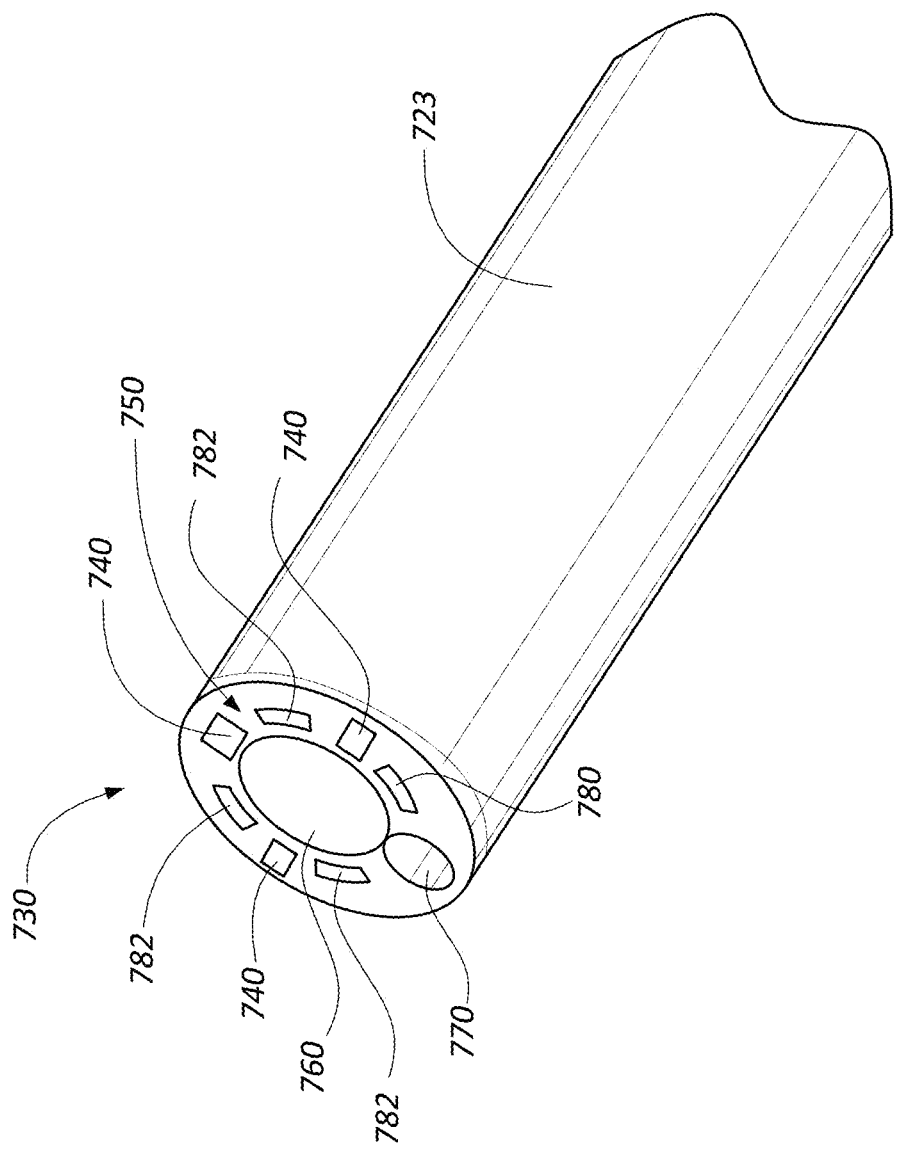
FIG. 8 is a close-up view of the tip of the borescope tube of FIG. 7.

As shown in FIG. 8, tip 730 and/or another component within borescope 700 may comprise various additional functional elements. Tip 730 comprises three LEDs 740 positioned in a circumferential manner relative to image sensor 760. Tip 730 may further comprise one or more through ports 770 that may extend at least partially up the length of the borescope tube 720 and/or the handle of borescope 700. Tip 730 may further comprise one or more lenses 750.

In order to facilitate one or more of the data storage/transmission aspects referenced above, tip 730 may further comprise a memory element 780 and one or more sensors 782. Examples of sensors that may be useful in gathering data, such as usage data, include temperature sensors, pressure sensors, impedance sensors, gyroscopes, timers, clocks, etc. In some embodiments, one or more of sensors 782 may comprise a second image sensor. Such image sensor may be used to capture images at select moments separate from the primary image sensor 760. Data obtained during a surgical procedure from such sensor(s) may be stored in memory element 780 and, ultimately, in some embodiments, may be sent to a similar memory element, such as memory element 810, located within dongle 800.

Figure 9:
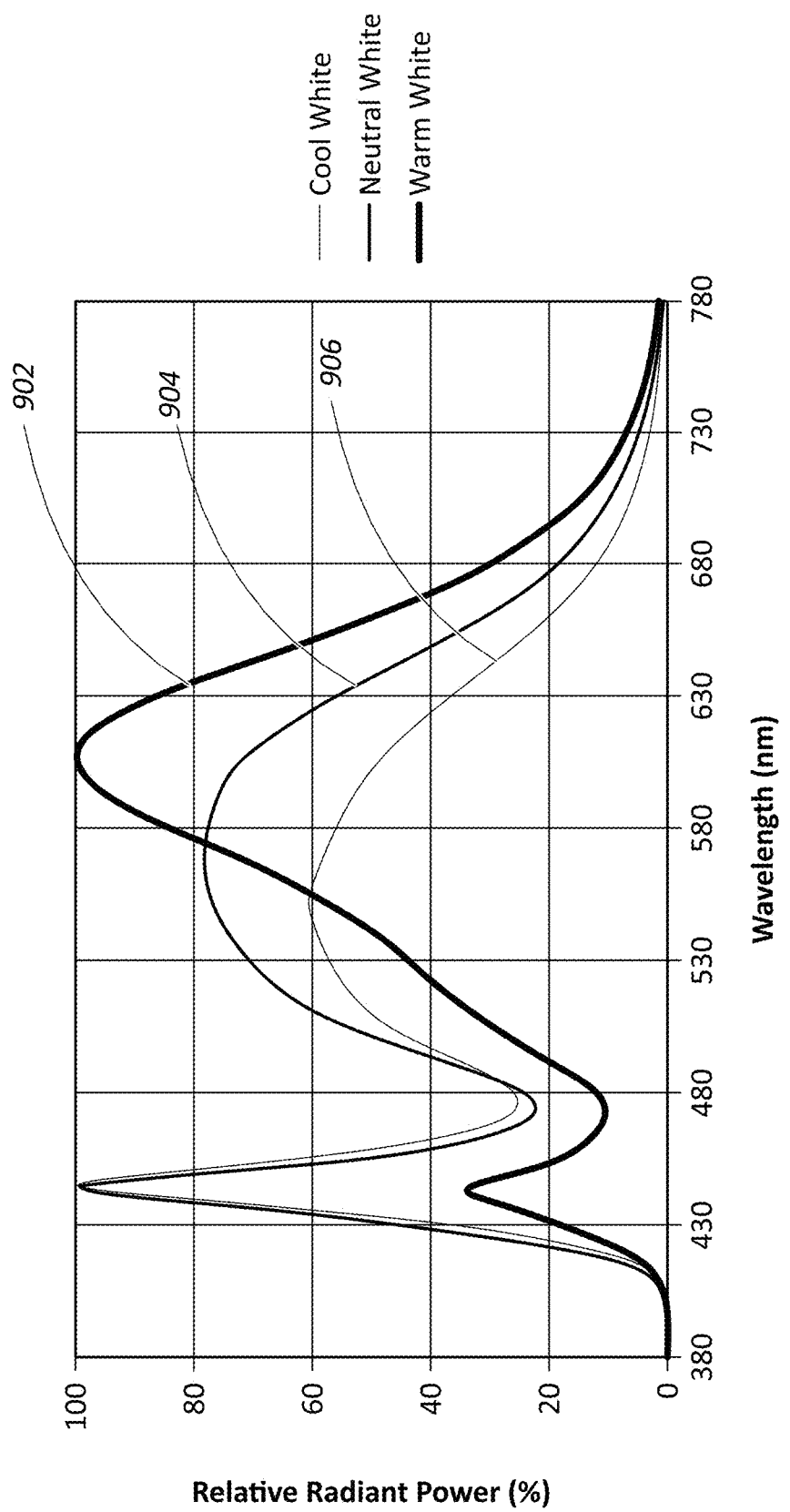
FIG. 9 is a chart depicting preferred spectral distributions for LEDs used with certain embodiments of borescopes disclosed herein.

FIG. 9 depicts a series of spectral distributions for LEDs that may be useful for certain embodiments of the present invention. Noteworthy is the fact that the spectral output of all three distributions—namely, distributions 902, 904, and 906—have no wavelengths in the infrared spectrum. The inventors have found light sources lacking in, or having relatively small contribution of, infrared radiation to be particularly useful spectral outputs for laparoscopes and other borescopes that may be used to image environments that may have particles in the vicinity of the imaging location, such as smoke. Such embodiments may therefore be particularly useful for imaging during cauterization and other electrosurgical procedures.

Thus, in preferred embodiments, laparoscopes or other borescopes may be provided with and/or used with LEDs or other light sources that are at least substantially lacking in radiation in the infrared portion of the spectrum. In some such embodiments, the laparoscopes or other borescopes may be entirely lacking in infrared radiation. In other embodiments, however, improved visibility in smoke or other similar conditions may still be provided by including some infrared radiation, so long as this amount is substantially reduced relative to typical laparoscope light sources, such as typical xenon lamps used in connection with laparoscopes currently. Thus, for example, in some embodiments, less than 20% of the total spectral output (as a percent of the total radiant energy, radiant intensity, and/or radiant flux) of the LED or other light source of the laparoscope or other borescope may be in the infrared spectrum. In some such embodiments, less than 10% of the total spectral output of the LED or other light source of the laparoscope or other borescope may be in the infrared spectrum. Again, in more preferred embodiments, the spectral output of the LED or other light source of the laparoscope or other borescope in the infrared spectrum may be zero, or at least substantially zero.

With reference again to FIG. 9, although any of the three spectral distributions depicted in the figure may be useful for improving imaging in smoke relative to the common current light sources, such as xenon lamps, the inventors have discovered that the most preferred distribution for this purpose is distribution 904 and the second most preferred distribution for this purpose is distribution 902. The inventors have discovered that shifting the distribution of visible light towards the blue end of the spectrum may be beneficial to being able to see clearly through smoke. Thus, as shown in FIG. 9, both distributions 902 and 904 have relative radiant maxima in the blue region of the visible spectrum.

In some embodiments, the spectral output of the LED or other light source of the laparoscope or other borescope may therefore include at least a local maximum in the blue region of the visible light spectrum, as is the case with all three of the spectral distributions 902, 904, and 906 shown in FIG. 9. In more preferred embodiments, the spectral output of the LED or other light source of the laparoscope or other borescope may have a global maximum in this region, as is the case with distributions 902 and 904.

The present inventors have discovered that imaging in such conditions may be improved by altering one or more of the following three parameters, as described herein. First, as shown in FIG. 9 and as discussed above, the spectral distribution of the LEDs or other light sources used in preferred embodiments may be skewed towards the color blue and away from longer wavelengths, such as infrared. Again, the inventors have discovered that longer wavelengths of light tend to interact more with smoke, and thus cause visibility problems. The most preferred embodiments of the invention therefore comprise an LED light that emits no wavelengths in the infrared spectrum, by design.

Figure 10A:
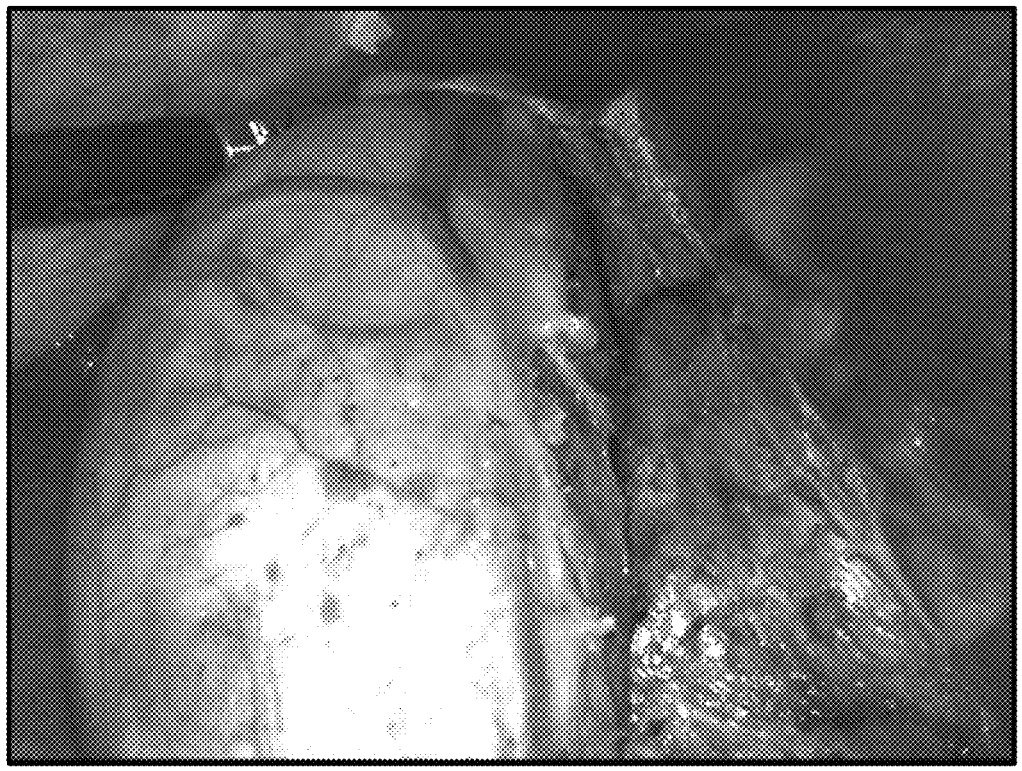
FIG. 10A is a photograph of patient anatomy during an electrosurgical procedure using a preferred embodiment of a borescope disclosed herein.
Figure 10B:
FIG. 10B is a photograph of patient anatomy during an electrosurgical procedure using existing laparoscope technology.

The improvement in visibility between a preferred embodiment of the invention and a typical prior art laparoscope light source is shown in FIGS. 10A and 10B. The photograph in FIG. 10B was taken using a typical xenon lamp light source. As shown in this photograph, the smoke from the electrocautery during a surgery makes it very difficult to see the underlying patient anatomy. By contrast, the photograph of FIG. 10A was taken using an LED light source having the spectral distribution 904 in FIG. 9. By altering the light source and/or other parameters, as discussed herein, the smoke (which is still present but not visible in the photograph of FIG. 10A) can be virtually eliminated from view, thereby substantially improving the ability of a surgeon to see and/or perform surgical procedures.

In addition to, or as an alternative to, providing such a preferred spectral distribution(s), the present inventors have discovered that decreasing the intensity of the light from the LEDs or other light sources reduces the amount of reflected light of the smoke. Two methods can be used to compensate for a lower intensity light source. One is to increase the aperture of the objective lens. This has the tradeoff of reducing the depth of focus. The other is to reduce the temporal noise floor of the image sensor. In some embodiments, both techniques may be used simultaneously. This may be accomplished, for example, by using cell phone optics. In some embodiments, the aperture size may therefore range from F #2.8 to F #2.0. A state-of-the-art image sensor with a low noise floor may also be used. Increasing the collection aperture size may further provide for better image quality, particularly in smoky conditions.

As another preferred technique/parameter for avoiding smoke or other similar imaging conditions, in some embodiments, the total amount of light or the total lumens of light of the LEDs or other light sources may be decreased relative to other typical light sources used during laparoscopic procedures or other such procedures. For example, in preferred embodiments, the LED or other light source of the borescope may be configured to deliver between about 20 and about 75 lumens of light from all LEDs or other light sources used in the borescope. In certain more preferred embodiments, the LEDs may be configured to deliver between about 25 and about 55 lumens of light from all LEDs or other light sources used in the borescope.

It will be understood by those having skill in the art that changes may be made to the details of the above-described embodiments without departing from the underlying principles presented herein. Any suitable combination of various embodiments, or the features thereof, is contemplated.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Throughout this specification, any reference to "one embodiment," "an embodiment," or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, inventive aspects lie in a combination of fewer than all features of any single foregoing disclosed embodiment. It will be apparent to those having skill in the art that changes may be made to the details of the above-described embodiments without departing from the underlying principles set forth herein.

Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. The scope of the present invention should, therefore, be determined only by the following claims.

The invention claimed is:

1. A medical borescope, comprising:
   a shaft comprising, at least in part, a material that is at least substantially electrically non-conductive material and at least substantially thermally non-conductive;
   a tip positioned at a distal end of the shaft, wherein the tip comprises:
      an image sensor configured to generate image data, and
      an array of LED light sources configured to deliver electromagnetic radiation in a spectrum that is delivered from the array of LED light sources lacking in infrared radiation, wherein the spectrum has a global maximum between 450 and 495 nm, and wherein the array of LED light sources is configured to collectively deliver between 20 and 75 lumens of visible light.

2. The medical borescope device of claim 1, wherein the shaft wholly comprises a material that is at least substantially electrically non-conductive material and at least substantially thermally non-conductive.

3. The medical borescope device of claim 1, wherein the shaft comprises a layer of material that is at least substantially electrically non-conductive material and at least substantially thermally non-conductive.

4. The medical borescope device of claim 3, wherein the layer comprises a sheath.

5. The medical borescope device of claim 1, wherein the material comprises a fiber-reinforced material.

6. The medical borescope device of claim 5, wherein the material comprises a fiber-reinforced, thermosetting polyester polymer.

7. The medical borescope device of claim 1, wherein the array of LED lights sources is configured to deliver between about 25 and about 55 lumens of visible light.

8. The medical borescope device of claim 1, wherein the tip further comprises an imaging aperture, and wherein the imaging aperture comprises an aperture size between F2.0 and F2.8.

9. The medical borescope device of claim 1, wherein the spectrum has a global maximum between 450 and 495 nm.

10. A medical borescope, comprising:
 a shaft; and
 a tip positioned at a distal end of the shaft, wherein the tip comprises an array of LED light sources configured to deliver electromagnetic radiation in which no more than about 20% of the total spectral output of the array of LED light sources is in the infrared spectrum, wherein electromagnetic radiation delivered from the array of LED light sources comprises a spectrum having a global maximum between 450 and 495 nm.

11. The medical borescope of claim 10, wherein the shaft comprises, at least in part, a material that is electrically non-conductive material and thermally non-conductive.

12. The medical borescope of claim 11, wherein the material comprises a fiber-reinforced polymer.

13. The medical borescope of claim 11, wherein the material comprises a unidirectional fiber.

14. The medical borescope of claim 10, wherein the material comprises an electrical conductivity less than about 5 S/m and a thermal conductivity of less than about 1 W/mK.

15. The medical borescope of claim 10, wherein the array of LED light sources comprises a plurality of distinct LED light sources, and wherein the array of LED light sources is configured to deliver electromagnetic radiation in which the spectral output in the infrared spectrum is zero.

16. The medical borescope of claim 10, wherein the array of LED light sources is configured to deliver between 20 and 75 lumens of visible light.

17. A method for medical imaging, the method comprising the steps of:
 inserting a medical borescope into a patient;
 illuminating a site of interest with electromagnetic radiation in an electromagnetic spectrum that is at least substantially lacking in infrared radiation, wherein the electromagnetic spectrum has a global maximum between 450 and 495 nm; and
 imaging the site of interest illuminated by the electromagnetic radiation using the medical borescope.

18. The method of claim 17, further comprising performing an electrosurgical procedure in which smoke is generated, wherein the electromagnetic spectrum is configured to at least substantially eliminate visibility of the smoke in one or more images generated during the imaging step.

19. The method of claim 17, wherein the electromagnetic radiation is generated using an array of LED light sources positioned at a tip of the medical borescope.

20. The method of claim 19, wherein the array of LED lights sources is configured to deliver between 25 and 55 lumens of visible light.

21. The method of claim 17, wherein the medical borescope comprises a laparoscope, and wherein the step of illuminating a site of interest comprises using between 20 and 75 lumens of unfiltered visible light.

* * * * *